United States Patent
Surridge et al.

(10) Patent No.: US 8,454,904 B2
(45) Date of Patent: Jun. 4, 2013

(54) BIOSENSOR CONTAINER

(75) Inventors: Nigel Surridge, Carmel, IN (US); Abner Joseph, Carmel, IN (US); Frank Chan, Sunnyvale, CA (US); Martin Gerber, Carmel, IN (US); Matt Sauers, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 855 days.

(21) Appl. No.: 12/181,519

(22) Filed: Jul. 29, 2008

(65) Prior Publication Data

US 2010/0025270 A1 Feb. 4, 2010

(51) Int. Cl.
*G01N 21/75* (2006.01)

(52) U.S. Cl.
USPC .............. 422/401; 422/500; 422/504; 436/14

(58) Field of Classification Search
USPC ....... 422/99, 102, 104, 401, 500, 504; 436/14
See application file for complete search history.

(56) References Cited

U.S. PATENT DOCUMENTS

| | | | |
|---|---|---|---|
| 4,731,726 A | 3/1988 | Allen | |
| 4,790,979 A | 12/1988 | Terminiello et al. | |
| 5,251,126 A | 10/1993 | Kahn et al. | |
| 5,307,263 A | 4/1994 | Brown | |
| 5,822,715 A | 10/1998 | Worthington et al. | |
| 5,989,917 A | 11/1999 | McAleer et al. | |
| 6,544,475 B1 | 4/2003 | Douglas et al. | |
| 6,656,114 B1 | 12/2003 | Poulsen et al. | |
| 6,840,904 B2 | 1/2005 | Goldberg | |
| 6,908,008 B2 | 6/2005 | Pugh | |
| 6,997,343 B2 | 2/2006 | May et al. | |
| 7,024,367 B2 | 4/2006 | Amano et al. | |
| 7,063,234 B2 | 6/2006 | Giraud | |
| 7,138,089 B2 | 11/2006 | Aitken et al. | |
| 7,212,925 B2 | 5/2007 | Genshaw | |
| 2003/0049849 A1 | 3/2003 | Mori et al. | |
| 2003/0125612 A1 | 7/2003 | Fox et al. | |
| 2003/0204313 A1 | 10/2003 | Ou-Yang et al. | |
| 2004/0007585 A1* | 1/2004 | Griffith et al. | ................ 221/232 |

(Continued)

FOREIGN PATENT DOCUMENTS

EP 1416417 5/2004

*Primary Examiner* — Michael Marcheschi
*Assistant Examiner* — Jonathan Hurst
(74) *Attorney, Agent, or Firm* — Krieg DeVault LLP

(57) ABSTRACT

A biosensor container comprising a housing defining an internal glucose test strip compartment. The housing has an engagement portion for retaining a detachable means for storing data, and the means for storing data has data stored thereon specific to a batch of glucose test strips. At least one of the housing and the means for storing data includes at least one data reading element that is externally accessible when the means for storing data is retained by the engagement portion of the housing. The container includes various fail safe features to prevent mishandling and insure the user obtains the correct results. The housing includes means for connecting to the bG meter only when the means for storing data is retained by the housing. The housing further includes means for dispensing glucose test strips only when the housing is in either of an attached-to meter mode or a stand-alone mode. In the attached-to-meter mode the means for storing data is retained by the housing and the housing is connected to a bG meter. In the stand-alone mode the means for storing data is detached from the housing and the housing is not connected to the bG meter.

13 Claims, 13 Drawing Sheets

U.S. PATENT DOCUMENTS

| | | |
|---|---|---|
| 2004/0073464 A1 | 4/2004 | Huang |
| 2005/0240119 A1 | 10/2005 | Draudt et al. |
| 2006/0003462 A1 | 1/2006 | Wang et al. |
| 2006/0182658 A1 | 8/2006 | Wu et al. |
| 2007/0016449 A1 | 1/2007 | Cohen et al. |
| 2008/0089812 A1* | 4/2008 | Uehata et al. ................ 422/104 |

* cited by examiner

BIOSENSOR CONTAINER

FIELD OF THE INVENTION

This application relates to an improved biosensor container, particularly a container for blood glucose strips.

BACKGROUND OF THE INVENTION

As the number of patients suffering from diabetes and similar medical conditions increases, self-monitoring of blood glucose wherein the patient monitors his or her blood glucose levels has become a common practice. The purpose of monitoring the blood-glucose level is to determine the concentration level and then to take corrective action, based upon whether the level is too high or too low, to bring the level back within a normal range. The failure to take corrective action can have serious medical implications. Glucose monitoring is a fact of everyday life for diabetic individuals, and the accuracy of such monitoring can literally mean the difference between life and death. Failure to test blood glucose levels accurately and on a regular basis can result in serious diabetes-related complications, including cardiovascular disease, kidney disease, nerve damage and blindness.

People with diabetes who intensively manage their blood sugar experience long-lasting benefits. The Diabetes Control and Complications Trial (DCCT) was a clinical study conducted from 1983 to 1993 by the National Institute of Diabetes and Digestive and Kidney Diseases (NIDDK). The DCCT compared intensive to conventional treatments. Patients on intensive treatment kept glucose levels as close to normal as possible with at least three insulin injections a day or an insulin pump, and frequent self-monitoring of blood glucose. Intensive treatment aimed to keep hemoglobin A1c (HbA1c), which reflects average blood glucose over a 2- to 3-month period, as close to normal as possible. Conventional treatment consisted of one or two insulin injections a day with once-a-day urine or blood glucose testing. The results of the DCCT study showed that keeping blood glucose levels as close to normal as possible slows the onset and progression of eye, kidney, and nerve diseases caused by diabetes. In fact, it demonstrated that any sustained lowering of blood glucose helps, even if the person has a history of poor control.

A number of glucose meters are currently available that permit an individual to test the glucose level in a small sample of blood. Many of the meter designs currently available make use of a disposable test strip which in combination with the meter measures the amount of glucose in the blood sample electrochemically. Lot-to-lot variation during the manufacture of disposable test strips requires that the user calibrate the system for each batch of strips. Given the ramifications of accurate monitoring, improvements in the apparatus and/or procedures to meter blood glucose are desired.

SUMMARY OF THE INVENTION

In one embodiment of the present invention there is a biosensor container. The biosensor container comprises a casing defining a compartment for receiving a plurality of glucose test strips. It also comprises means for storing data with data stored thereon of at least one of strip lot information and strip family specific calibration information. The means for storing data is sized to be at least partially received within and detachably connected to an engagement portion of the casing. The biosensor container also includes a means for dispensing the glucose test strips only when the container is in either of a first mode or a second mode. In the first mode the means for storing data is connected to the casing and the casing is docked to a meter. In the second mode the means for storing data is detached from the casing and the casing is not docked to the meter. At least one of the casing and the means for storing data includes at least one data reading element that is externally accessible when the means for storing data is connected to the engagement portion of the casing. The at least one data reading element communicating with the means for storing data to access the data stored thereon.

One refinement of the embodiment is when the compartment is pre-filled with a first batch of glucose test strips from the factory. The data stored on the means for storing data includes calibration information for the first batch of glucose test strips.

In another refinement of the embodiment the compartment is externally accessible to fill or refill the compartment with a plurality of glucose test strips.

In another refinement of the embodiment, in combination with the meter, the data stored on the means for storing data is automatically transferred from the means for storing data to the meter in the first mode.

In another refinement of the embodiment, in combination with the bG meter, the glucose test strips are directly dispensed into the bG meter in the first mode.

In another refinement of the embodiment, in combination with the bG meter, the casing is configured so that it can only be attached to the bG meter when the means for storing data is connected to the casing.

In another refinement of the embodiment, in combination with the bG meter, the means for storing data includes additional data storage capacity. The bG meter writes information onto the additional data storage capacity. The information is selected from the group consisting of the number of strips used, bG results from at least one of the test strips, time and date of bG results, meter status, any error codes received during or before or after bG testing, and additional data manually input into the meter.

In another embodiment of the present invention there is an apparatus comprising a bG meter; a biosensor container comprising a casing defining an interior volume for a batch of glucose test strips; and a means for storing data with data stored thereon relating to the batch of glucose test strips. The data includes at least one of strip lot information and strip family specific calibration information. The means for storing data is detachably retained by the biosensor container. The container is configured to only dispense glucose test strips when the container is in either of an attached-to meter mode or a stand-alone mode. In the attached-to-meter mode the means for storing data is connected to the container and the container is connected to the bG meter. In the stand-alone mode the means for storing data is separated from the container and the container is not connected to the bG meter.

In one refinement of the embodiment the data stored on the means for storing data is automatically transferred from the means for storing data to the bG meter in the attached-to-meter mode.

In another refinement of the embodiment the biosensor container includes means for dispensing the glucose test strips directly into the meter in the attached-to-meter mode.

In another refinement of the embodiment the container is configured to connect to the bG meter only when the means for storing data is connected to the container.

In another refinement of the embodiment the casing of the biosensor container defines an externally accessible portal that may be opened to fill the compartment with glucose test strips.

In another refinement of the embodiment the means for storing data includes additional data storage capacity. The bG meter writes information onto the additional data storage capacity. The information is selected from the group consisting of the number of strips used, bG results from at least one of the test strips, time and date of bG results, meter status, any error codes received during or before or after bG testing, and additional data manually input into the meter.

In another embodiment of the present invention there is a biosensor container comprising a housing defining an internal glucose test strip compartment. The housing has an engagement portion for retaining a detachable means for storing data, and the means for storing data has data stored thereon specific to a batch of glucose test strips.

In one refinement of the embodiment at least one of the housing and the means for storing data includes at least one electrical contact that is externally accessible when the means for storing data is retained by the engagement portion of the housing. The at least one electrical contact is electrically connected to the means for storing data to access the data stored thereon.

In another refinement of the embodiment the housing includes means for connecting to the bG meter only when the means for storing data is retained by the housing.

In another refinement of the embodiment the housing further includes means for dispensing glucose test strips only when the housing is in either of an attached-to meter mode or a stand-alone mode. In the attached-to-meter mode the means for storing data is retained by the housing and the housing is connected to a bG meter. In the stand-alone mode the means for storing data is detached from the housing and the housing is not connected to the bG meter.

In another refinement of the embodiment the means for dispensing inserts the glucose test strips directly into the bG meter in the attached-to-meter mode.

In another refinement of the embodiment the housing defines an externally accessible portal that may be opened to insert glucose test strips into the internal compartment.

In another refinement of the embodiment, in combination with the bG meter, the means for storing data includes additional data storage capacity. The bG meter writes information onto the additional data storage capacity. The information is selected from the group consisting of the number of strips used, bG results from at least one of the test strips, time and date of bG results, meter status, any error codes received during or before or after bG testing, and additional data manually input into the meter.

DETAILED DESCRIPTION OF THE PREFERRED EMBODIMENTS

Figure 1:
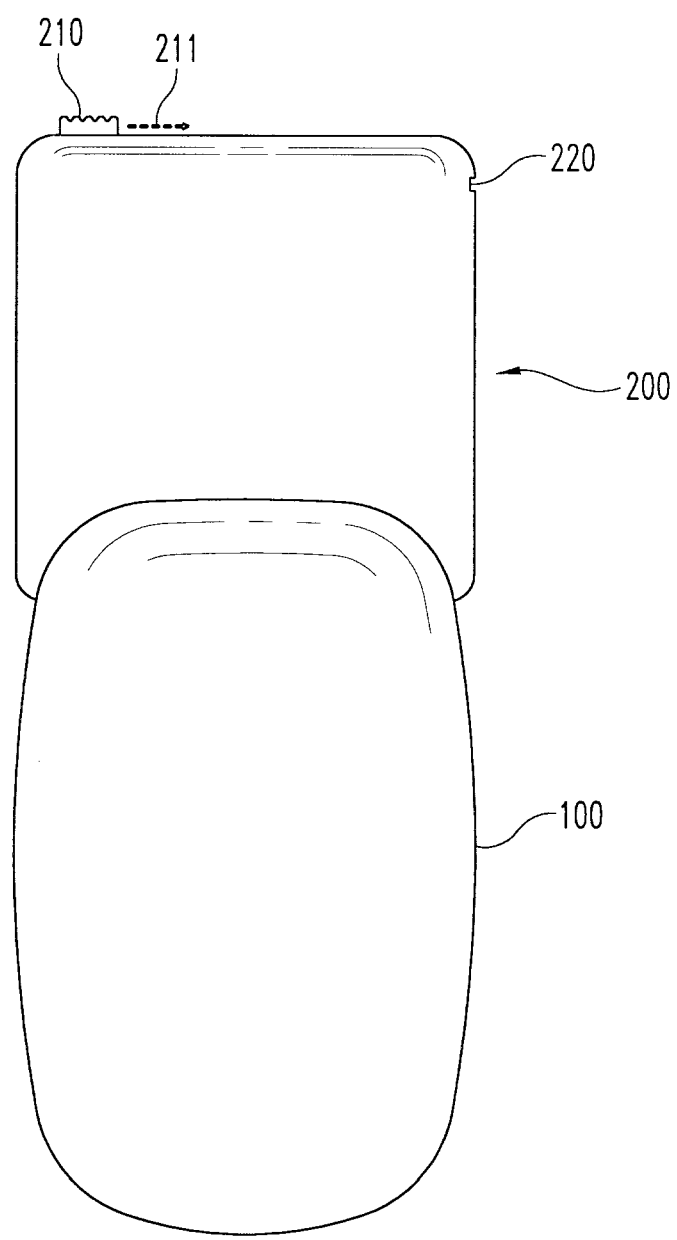
FIG. 1 is a top view of an end mounted biosensor container and bG meter according to one embodiment of the present invention.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As previously noted, accurate glucose monitoring is a potentially life and death issue for diabetic individuals. Glucose monitoring apparatus and procedures are preferably designed to be as simple and error free as possible. Handling a plurality of components during bG (blood Glucose) testing and insulin dosing is one major problem for people with diabetes. Thus, it would be preferable to simplify ease of use of apparatus during bG testing. Potential implementations according to at least some embodiments of the present invention might include combining things in simple packaging so that steps are not forgotten, or so that all handling steps are automated or at least intuitively enforced. Handling of strips, as well as programming the bG monitor with strip specific calibration information can be quite problematic, and thus is preferably automated. Lot-to-lot variation during the manufacture of test strips requires that the user calibrate the system for each batch of strips.

Existing test strips for glucose monitoring are available in a variety of packaging. Calibration information concerning the test strips must be provided to the meter. In one existing packaging, test strips are delivered in a vial with a removable stopper, which might be hinged to the vial. In one form the vial's code information from the strip might be transferred to the meter by way of a code number that is manually entered into the meter.

In another existing packaging, there is packaging of strips in foil wraps, 1 or also 10 at a time are used. In case of 10 strips in a foil pack, those packs of 10 are inserted as one pack into a meter device, and the meter device dispenses the strips into a measurement zone. An existing alternative is the use of a drum with 17 strips inside, the drum being inserted into a bG meter, the meter dispensing the strips into the measurement position. In the case of the 10-strip wrap or the drum, a bar code containing the lot specific information might be automatically read by the meter. Yet another alternative uses one meter per 50 or 100 strips, thus the instrument is pre-programmed with the lot calibration information. However, this results in a large amount of electronic waste. In one device 100 strips are stored in a stacked form in a meter. After all 100 strips are used by the meter, the whole device is discarded.

Various embodiments of the present invention relate to an easy to use primary pack for blood glucose strips. Improved blood glucose strip packaging is preferred as well as preferably implementing transfer of calibration information transparently for the end user. At least one embodiment of the present invention might include automating various steps of handling a plurality of components during bG testing and insulin dosing using a novel biosensor container, and combination of the same with a meter. Additionally, the strip packaging is preferably "backwards" compatible with existing bG meters, allowing universal replacement of current strip packaging design.

There is disclosed herein a simple packaging of strips, that can be used in a stand-alone mode or in an attached-to-meter mode. The packaging of strips preferably permits easy dispensing of the strips, either directly into the meter, or alternatively out of the packaging, allowing the end user to decide when and how to insert the strip into the meter, or back into the dispenser. The strip lot information is encoded in an electronic chip (also known as a code key) and is transferred automatically when the biosensor container is in the attached-to-meter mode. Alternatively, the chip can be separated from the container and inserted by the user into a stand-alone meter. Again the strip lot information would preferably be transferred automatically from the chip to the bG meter when the code chip is inserted by the user. The strip container preferably includes multiple fail-safes to guard from mishandling and the potential of getting wrong results by the user.

Figure 2:
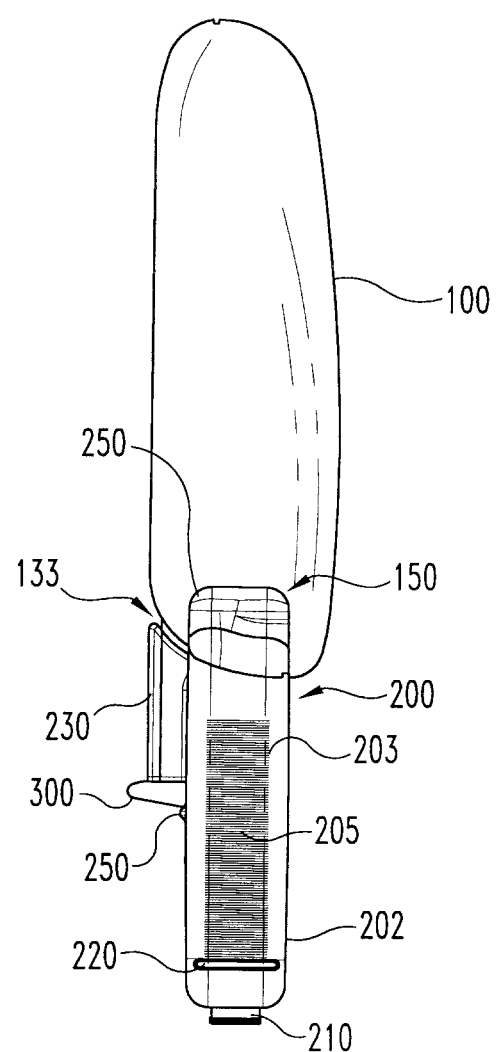
FIG. 2 is a side partial cross-sectional view of FIG. 1.
Figure 3:
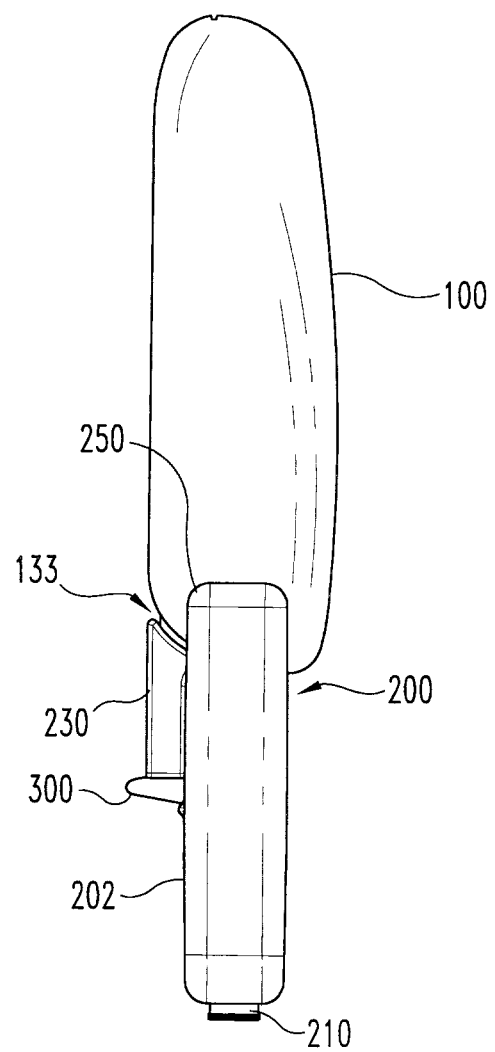
FIG. 3 is a side view of FIG. 1.
Figure 4:
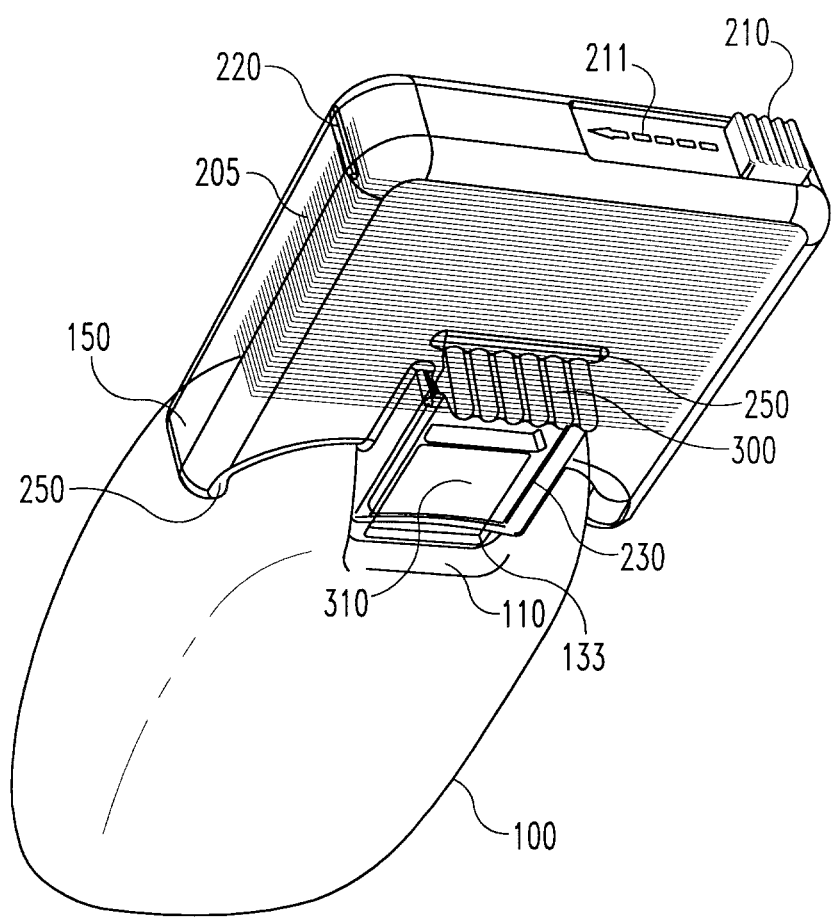
FIG. 4 is a bottom partial cross-sectional perspective view of FIG. 1.
Figure 5:
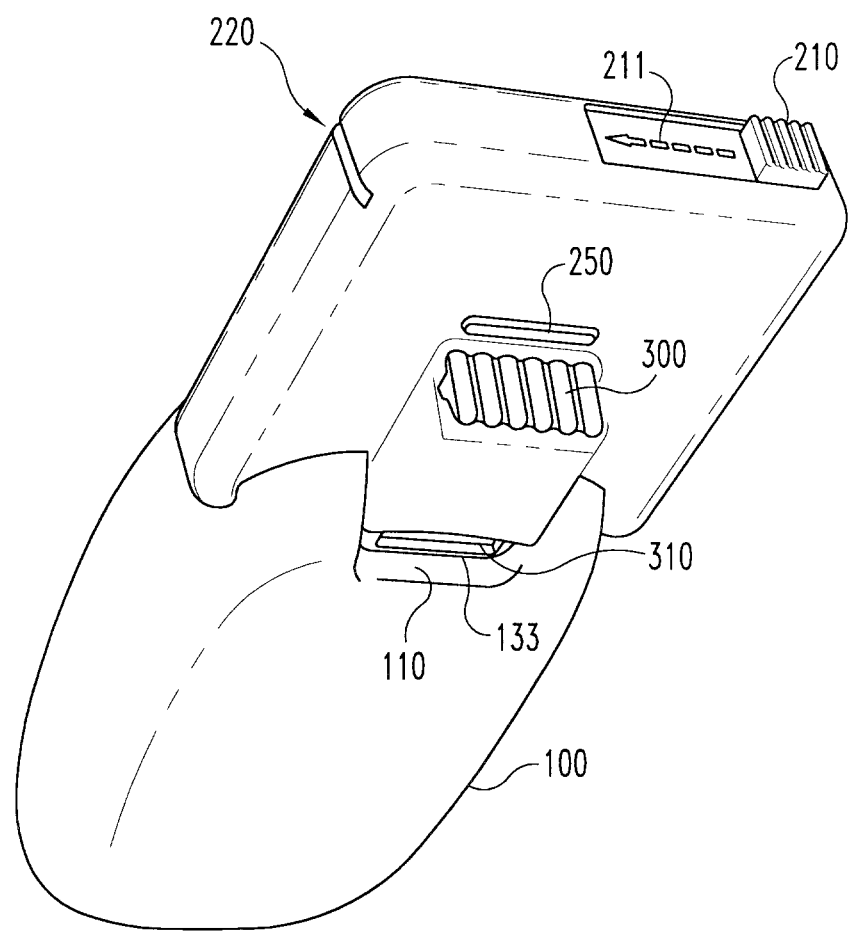
FIG. 5 is a bottom perspective view of FIG. 1.
Figure 6:
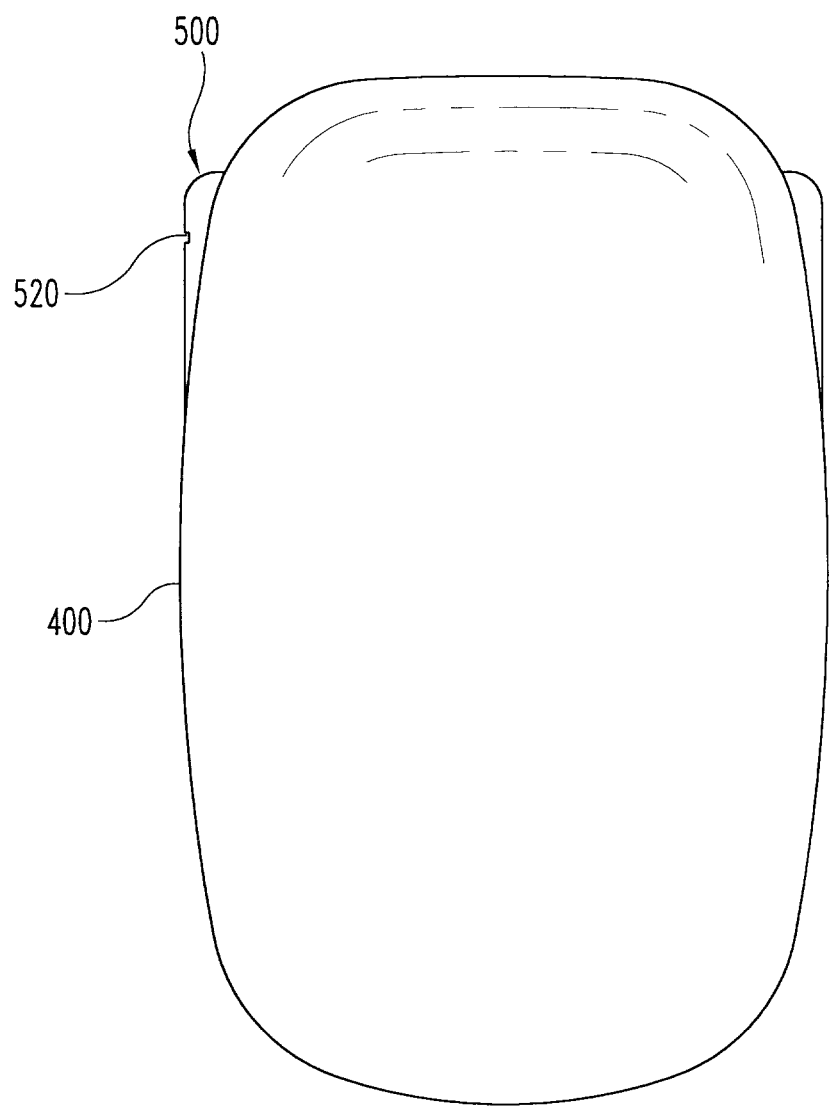
FIG. 6 is a top view of a side mounted biosensor container and bG meter according to another embodiment of the present invention.

With reference to FIGS. 1-5 there is illustrated one embodiment of the present invention of a biosensor container 200 mounted on the end of a meter 100. As discussed herein the meter 100 is described herein with reference to a bG meter and the biosensor container 200 is described as containing and dispensing glucose test strips. However, the meter and biosensor container might relate to other analytes. The meter 100 includes a microprocessor controlled display (not illustrated) for the user to review the results of the bG test strips, as well as whatever other information the meter is programmed to provide the user. As illustrated the meter 100 includes a slot 150 to which a flange or tab 250 of the container 200 is mounted to removably connect the meter 100 to the container 200. It should be understood that it is contemplated as within the scope of the invention that the meter 100 might include protrusions such as flanges or tabs, and the container a slot into which the protrusions are removably mounted. Furthermore, as illustrated in FIG. 4, the meter 100 preferably includes a recess or slot 110 configured to receive the code key 300.

The strip dispenser 200 includes a casing 202 that defines an internal compartment 203. The internal compartment 203 is sized to receive at least one, and preferably a plurality of glucose test strips 205. A sliding dispenser mechanism 210 translates as indicated by arrow 211 to cause the container 200 to eject a test strip 205 from strip outlet 220. As illustrated in, for example, FIGS. 2 and 3, the container 200 includes a portion 230 for receiving therein at least a portion of the code key 300. The code key 300 may be retained by either or both of a frictional fit within portion 230 and/or a protruding retention portion or bump 250. The code key 300 includes a printed circuit board 310 attached thereto that contains data that is uploaded to the meter through at least one electrical contact at interface 133. Interface 133 is preferably located in recess 110.

Electrical contact(s) may be present either on the code key 300 or the container 200 or both. That is to say, at least one of the casing and the code key includes at least one electrical contact that is externally accessible when the code key is retained by the engagement portion of the casing. Thus, a portion of the code key 300 might extend through engagement portion 230 of container 200 and interface directly with the meter 100. Alternatively, electrical contacts on the code key 300 might be internal to the container 200, with internal electrical connections extending from electrical contacts on the code key to electrical contacts that are externally accessible on the outer surface of the container 200. However, as illustrated in FIGS. 2 and 3, code key 300 preferably interfaces with meter 100 directly when container 200 is mounted thereto. In either event, the externally accessible electrical contact(s) interface with corresponding contacts on the meter 100, permitting the meter 100 to access and/or upload the data stored on the code key 300. Additionally, as will be discussed further below, the code key 300 preferably includes additional data storage capacity to which the meter 100 may write information including, but not limited to, information regarding bG results. However, is should be understood that alternative means for storing data (other than a code key) are contemplated as within the scope of the invention including, but not limited to, an apparatus with an optical bar code thereon. In such situations the container, instead of having electrical contacts, will include some other form of data reading element compatible with the means for storing data to access data stored thereon.

Figure 7:
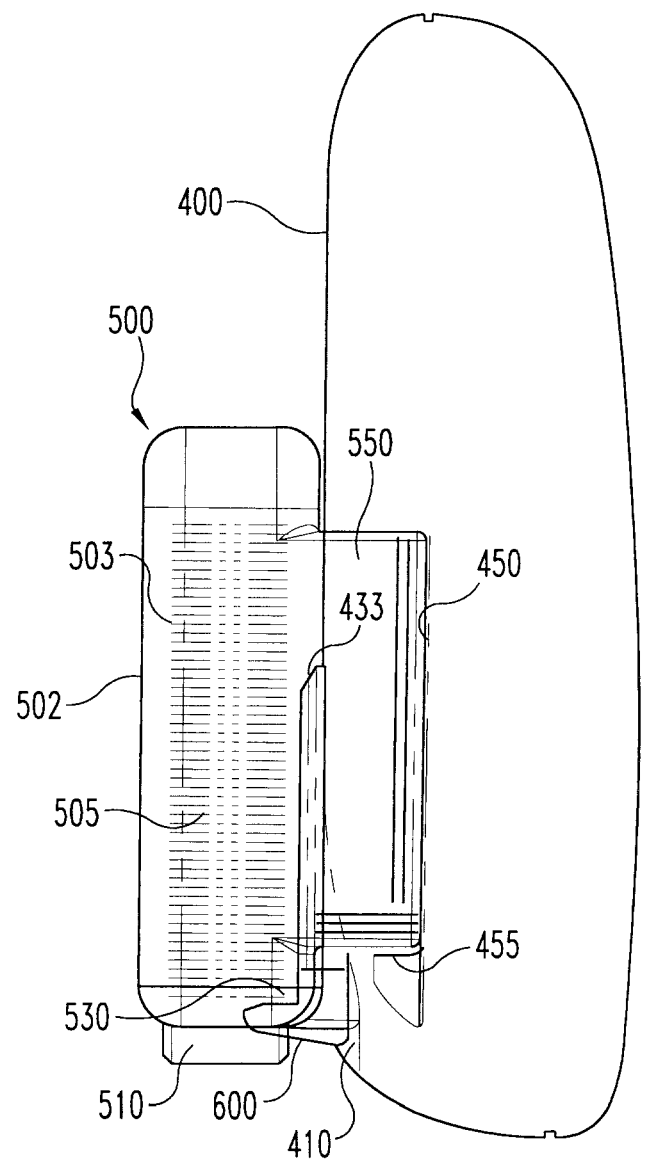
FIG. 7 is a side partial cross-sectional view of FIG. 6.
Figure 8:
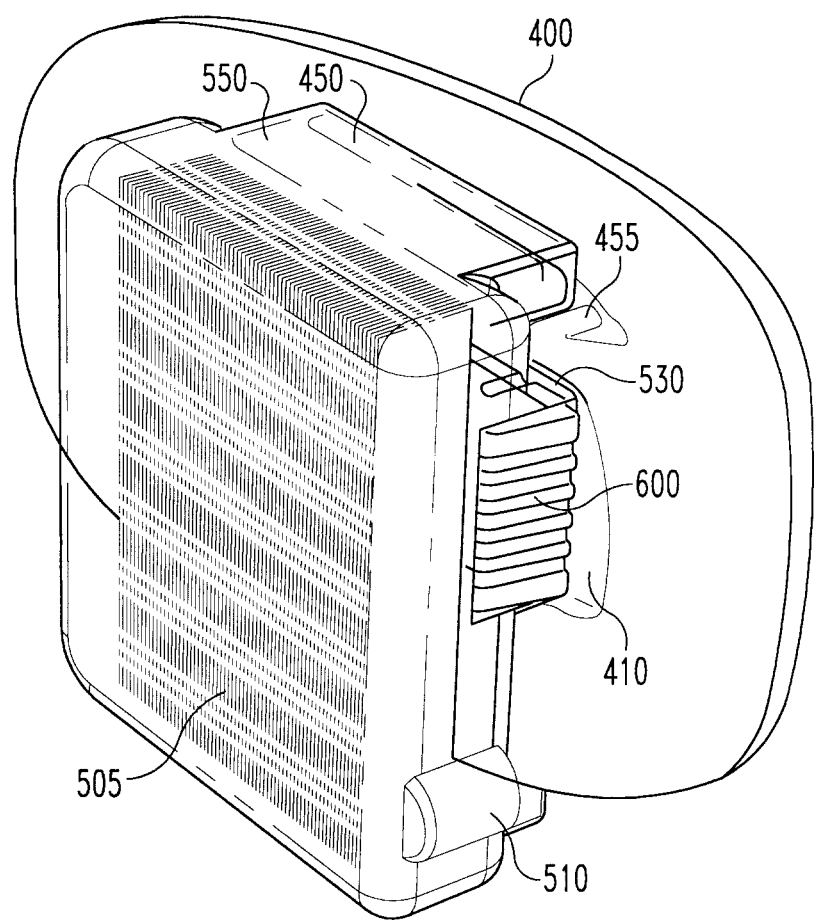
FIG. 8 is a perspective view of FIG. 7.
Figure 9:
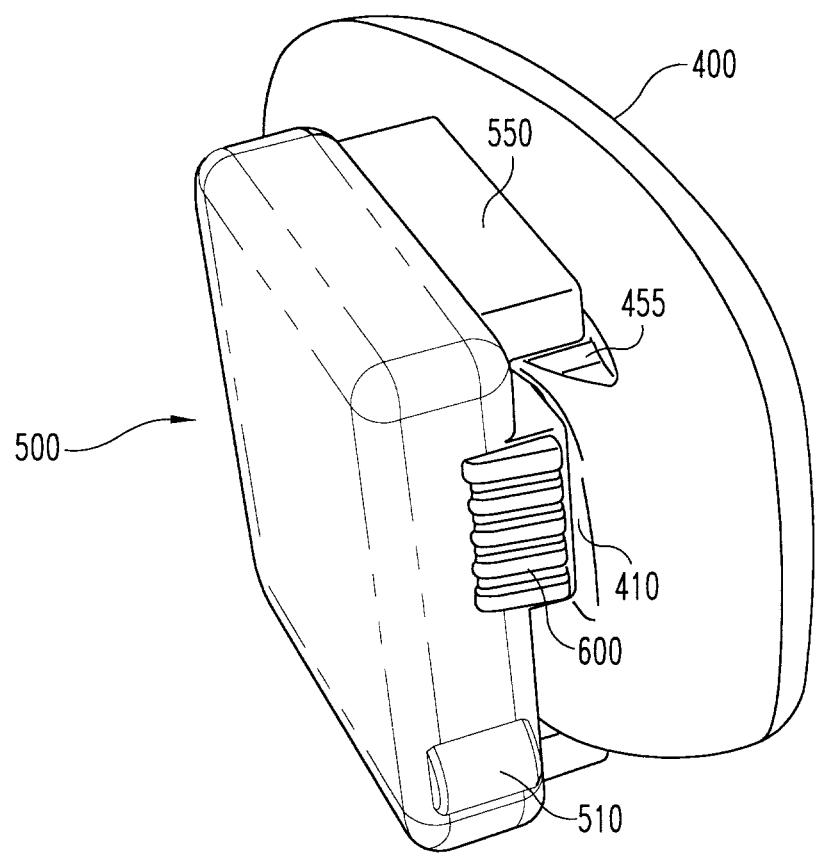
FIG. 9 is a bottom perspective view of FIG. 6.

With reference to FIGS. 6-9 there is illustrated one embodiment of the present invention of a biosensor container 500 mounted on the side of a meter 400. As discussed herein the meter 400 is described herein with reference to a bG meter and the biosensor container 500 is described as containing and dispensing glucose test strips. However, the meter and biosensor container might relate to other analytes. The meter 400 includes a microprocessor controlled display (not illustrated) for the user to review the results of the bG test strips, as well as whatever other information the meter is programmed to provide the user. As illustrated the meter 400 preferably includes a tongue and groove engagement slot 450 and a protrusion 455 for retaining a flange or tab 550 of the container 500 mounted to removably connect the meter 400 to the container 500. It should be understood that it is contemplated as within the scope of the invention that the meter 400 might include the flanges or tabs, and the container a slot into which the flanges or tabs are removably mounted. Furthermore, as illustrated in FIGS. 7 and 8, the meter 400 preferably includes a recess or slot 410 configured to receive the code key 600.

The strip dispenser 500 includes a casing 502 that defines an internal compartment 503. The internal compartment 503 is sized to receive at least one, and preferably a plurality of glucose test strips 505. A dial wheel dispenser mechanism 510 rotates to cause the container 500 to eject a test strip 505 from a strip outlet 520. As illustrated in, for example, FIGS. 7 and 8, the container 500 includes a portion 530 for receiving therein at least a portion of the code key 600. Alternatively, it is contemplated as within the scope of the invention that the code key may simply be adjacent to the container 500, being sandwiched between the container 500 and the meter 400. However, the code key 600 is preferably retained by a portion 530 and/or a retention protrusion. The code key 600 includes a printed circuit board attached thereto that contains data that is uploaded to the meter through at least one electrical contact at interface 433. The interface 433 is shown as being at an end of the code key 600, but might instead be at any of a number of locations along the length of the code key. Interface 433 is preferably located in recess 410. Additionally, as discussed previously with respect to the embodiment of FIGS. 1-5, the connection between the code key 600 and the meter 400 may be direct or indirect. Thus, the electrical contact(s) on the code key 600 might be electrically connected to corresponding electrical contact(s) on the meter via electrical connections in the strip container 500.

As discussed above with respect to the figures, embodiments of the present invention include a blood glucose strip container. The strip container might come pre-filled with a number of strips from the factory. Alternatively, the strip container might be filled (or refilled) with a cartridge of strips (preferably including desiccant) by the user. Such strips might be delivered to the user, for example, in a separate cartridge with desiccant in a foil wrap type packaging, along with an associated electronic chip. Consequently, various embodiments of the strip container of the present invention preferably include a movable (or removable) access panel to permit the internal glucose strip compartment to be externally accessible. A wide variety of access portals are contemplated as within the scope of the invention. Such access portal might be at the end of the strip container spaced apart from the meter, or adjacent the meter, or on one of the sides of the strip container. In one variation the end of the strip container at which glucose test strips are dispensed is a hinged lid that rotates to access the internal compartment. In other variations the access portal might be closed by a movable (as by rotating within the housing of the strip container) or removable access panel.

The strip container can be used in either a stand-alone mode or an attached-to-meter mode. In the stand alone mode a trigger (such as a sliding mechanism or dial wheel) is operated to release a glucose test strip to the user. The user then can insert the strip into a meter. Alternatively, the strip container can be used in an attached-to-meter mode. In one embodiment the attached-to-meter mode of the strip is preferably directly transferred into the meter automatically by a mechanical slider or similar device (such as a dial wheel) by the user. However, it is also contemplated as within the scope of the invention that in the attached-to-meter mode the strip can be dispensed outside, and manually inserted by the user into a bG meter.

The biosensor container includes an electronic chip or code key with data stored thereon relating to the glucose test strips. The data stored thereon preferably includes at least one, and even more preferably both, of the strip lot and strip family specific calibration information. The data stored on the code key is preferably transferred automatically from the code key into the bG meter when the strip container is in the attached-to-meter mode. Alternatively, in the stand-alone mode of operation the code key can be removed from the strip container and can be manually inserted into a bG meter in order to transfer the code key information. Consequently, in the stand-alone mode of operation the strip container may also find use with older versions of bG meters that are not configured to permit attachment of the strip container to the bG meter. That is to say, the separate strip container can be used to accept the foil wrapped cartridge, providing for a solution that is backwards compatible with existing products in which the user needs to remove the code key from the strip container for direct insertion into the bG meter (and transfer of the data stored thereon to the bG meter).

Various embodiments of the present invention are preferably implemented with one or more failsafe and user error preventing features. One example of such a feature is configuring the container so that it can only be attached to a meter when the code key is present in the container so that a successful data transfer occurs. Another example of a failsafe and/or user error preventing feature is a container in which glucose test strips can only be dispensed in one of two modes. That is to say, in the attached-to-meter mode a strip can only be dispensed from the container when the code key is in the container and the container is docked to the bG meter. Similarly, in the stand-alone mode a strip can only be dispensed from the container when the code key is removed from the container and the container is not attached or docked to the bG meter. Examples of implementing several possible such failsafe and/or user error preventing features will now be discussed as illustrated in FIGS. 10-24.

Figure 10:
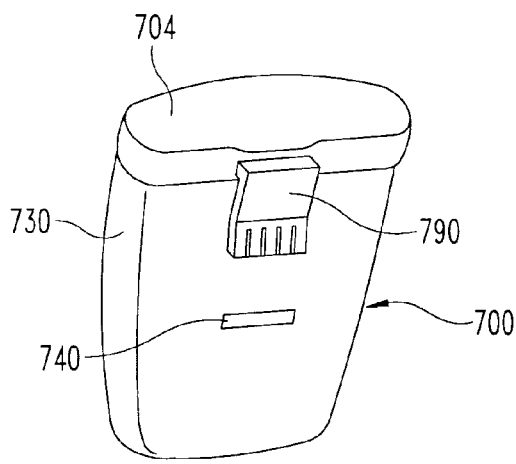
FIG. 10 is a side perspective view of an embodiment illustrating a code key latch inserted to prevent the container from being opened.
Figure 11:
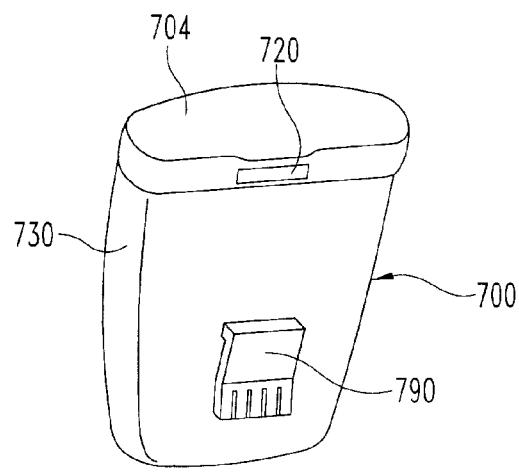
FIG. 11 is a side perspective view of FIG. 10 with the code key latch inserted to permit the container to be opened.

With reference to FIGS. 10-11 there is illustrated a code key 790 installed in a container 700. With reference to FIG. 10 the code key 790 is installed in the lid 704 of container 700, preventing the container lid 704 from opening. The code key penetrates the slot 720 of lid 704 of container 700, and extends partially into the body 730 of the container 700. To allow access to the biosensors (allow the container lid 704 to be opened), the code key 790 must be removed from slot 720. For the situation in which the container 700 is used as a stand-alone, the code key 790 is installed into the meter (not illustrated). For the situation in which the container 700 is to be used as an attached unit, the code key 790 is installed (see FIG. 11) into the slot 740 on lower portion of the body 730 of container 700. The code key 790 is preferably designed as the latch to allow the container 700 to be attached and lock to the meter, and without it the container 700 cannot be attached.

Figure 12:
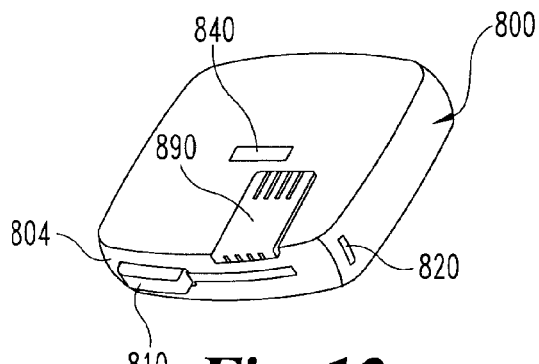
FIG. 12 is a perspective view of an embodiment illustrating a code key latch inserted to prevent the sliding dispensing mechanism from dispensing test strips.
Figure 13:
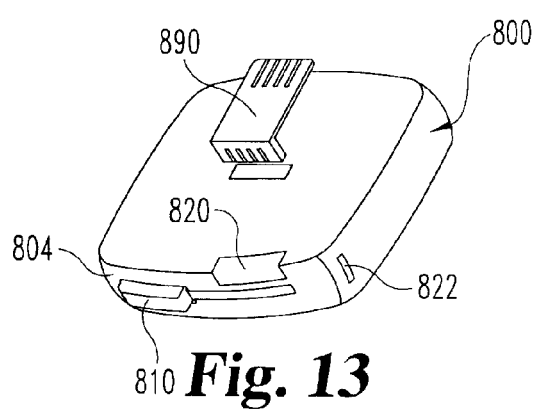
FIG. 13 is a perspective view of an embodiment illustrating a code key latch inserted to permit the sliding dispensing mechanism to dispense test strips.
Figure 14:
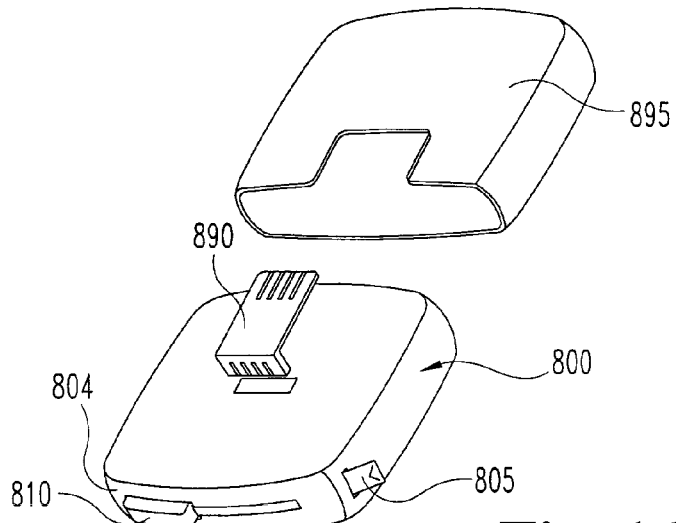
FIG. 14 is a perspective view of the embodiment of FIGS. 12 and 13 illustrating use of the code key latch to attach the container to a meter.

With reference to FIGS. 12-14, there is illustrated a similar principle applied to a dispenser type container 800. The code key 890 is installed in the slot 820 of upper portion 804 of the container 800 preventing the sliding dispenser mechanism 810 from operating to dispense strips 805 out strip outlet 822. To allow access to the biosensors (allow the sliding dispenser mechanism 810 to move) the code key 890 must be removed (container to be used as a stand-alone) or installed into the slot 840 on the lower portion of the container 800 (container to be used as an attached unit). When inserted in slot 840 the code key 890 is preferably designed as a latch to allow the container 800 to be attached and locked to the meter 895, and without it the container cannot be attached to the meter.

Figure 15:
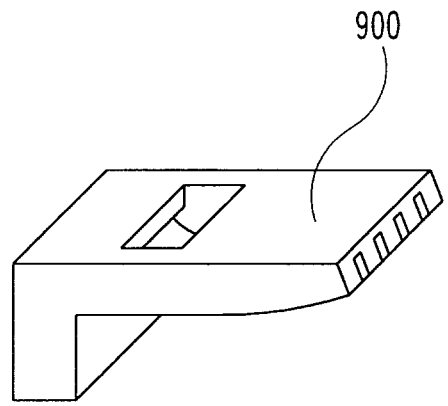
FIG. 15 is a side perspective view of a center snap code key latch design.
Figure 16:
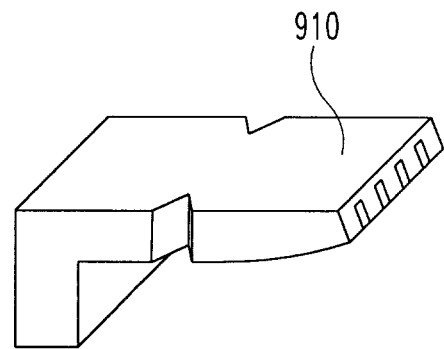
FIG. 16 is a side perspective view of an edge snap code key latch design.
Figure 17:
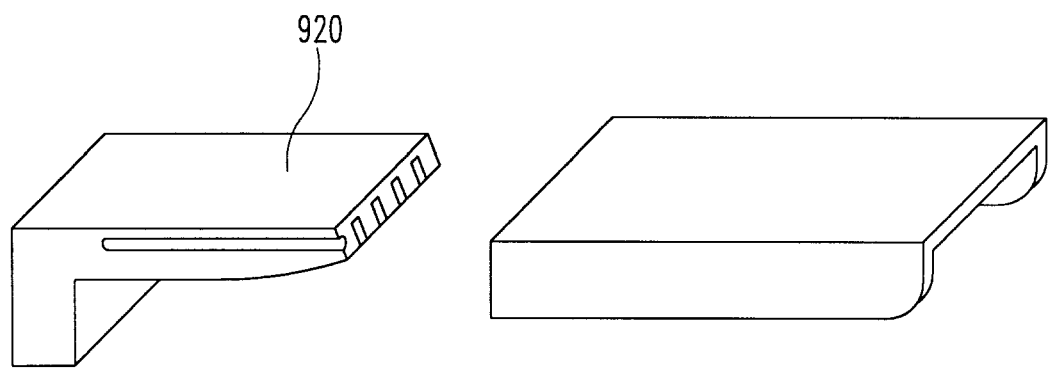
FIG. 17 is a side perspective view of a slide on code key latch design.
Figure 18:
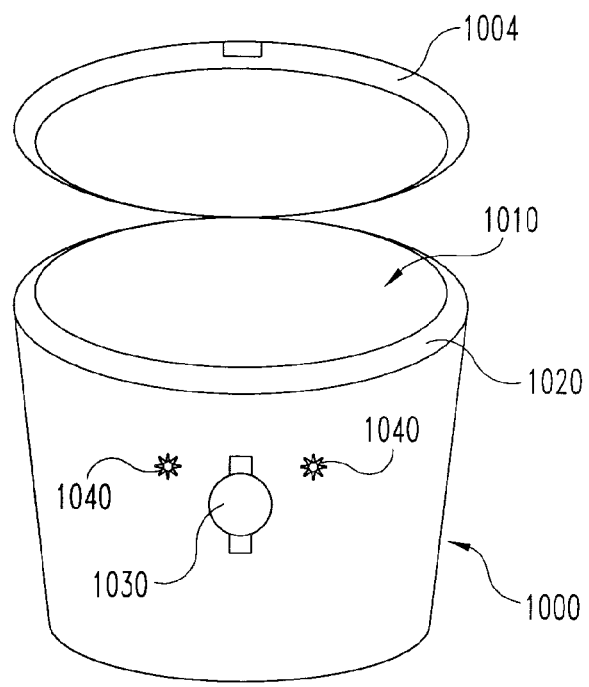
FIG. 18 is a side view of another embodiment of a biosensor container having an attached configuration and a stand-alone configuration.
Figure 19:
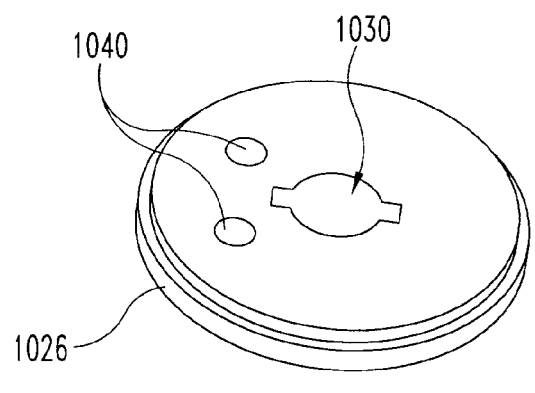
FIG. 19 illustrates aspects of the locking mechanism compartment of the embodiment of FIG. 18.
Figure 20:
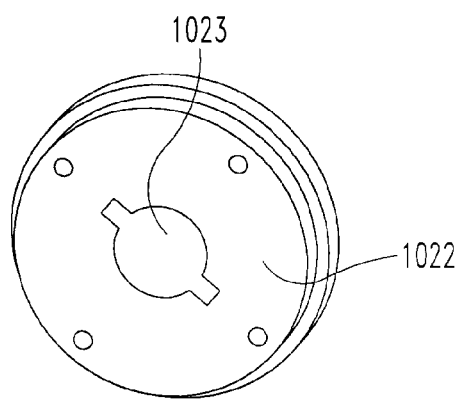
FIG. 20 illustrates the locking plate of the embodiment of FIG. 18.
Figure 21:
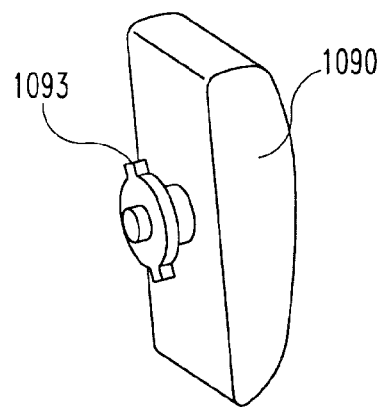
FIG. 21 illustrates a side perspective view of a code key latch for use with the embodiment of FIG. 18.
Figure 22:
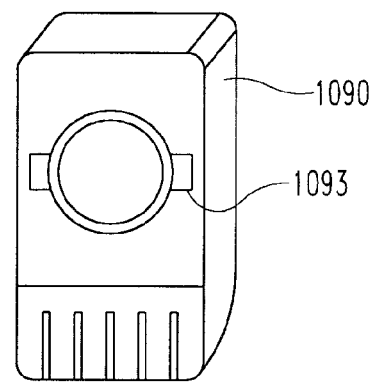
FIG. 22 illustrates an end view of a code key latch for use with the embodiment of FIG. 18.

With reference to FIGS. 15-17, there are illustrated examples of different code key latch designs. With reference to FIG. 15, there is illustrated a code key 900 with a center snap latch design. With reference to FIG. 16, there is illustrated a code key 910 with an edge latch snap design. With reference to FIG. 17, there is illustrated a code key 920 with a slide-on latch design.

With reference to FIGS. 18-24 there is illustrated another embodiment of one or more failsafe and user error preventing features. The biosensor container 1000 includes two compartments. The first compartment 1010 is for the storage of biosensors. The second compartment 1020 is for the locking mechanism. The biosensor compartment 1010, similar to a vial, seals the biosensors from the environment. The locking mechanism compartment 1020 houses (FIGS. 19 and 20) the locking plate 1022 and a wave spring 1024. The locking plate 1022 has a raised lip 1026 over half of the circumference of the round plate and is in the lock position when the lip area is engaged over the container latch (similar to a knife lock on file boxes). The locking plate defines a receptacle 1023 that corresponds to a protrusion 1093 of the code key latch 1090 (see FIGS. 21 and 22). Rotation of the code key latch 1090 permits the container 1000 to be changed from a stand-alone configuration (see FIG. 23) to an attaching configuration (see FIG. 24).

Figure 23:
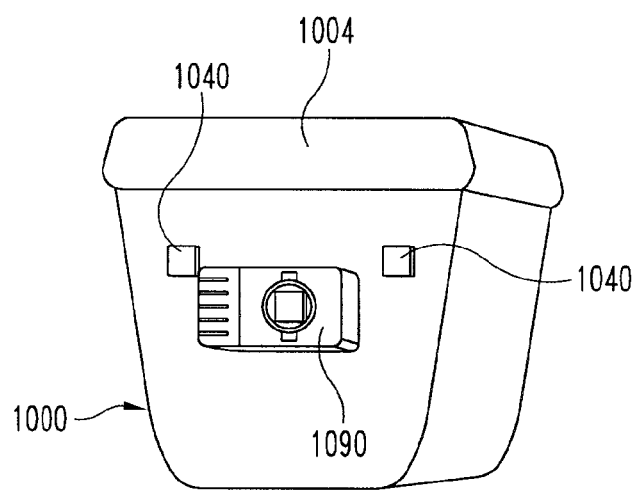
FIG. 23 illustrates a side view of the embodiment of FIG. 18 with the code key latch rotated to unlock the container.

The stand-alone configuration of the container 1000 is illustrated in FIG. 23. To access the biosensor container 1000 as a stand-alone, the code key 1090 is rotated to the 90 degrees position. This rotates the locking plate 1022 to the open position and aligns the plate 1022 to enable removal of code key 1090 from the container 1000. The code key 1090 can now be removed and inserted into the meter (not illustrated).

Figure 24:
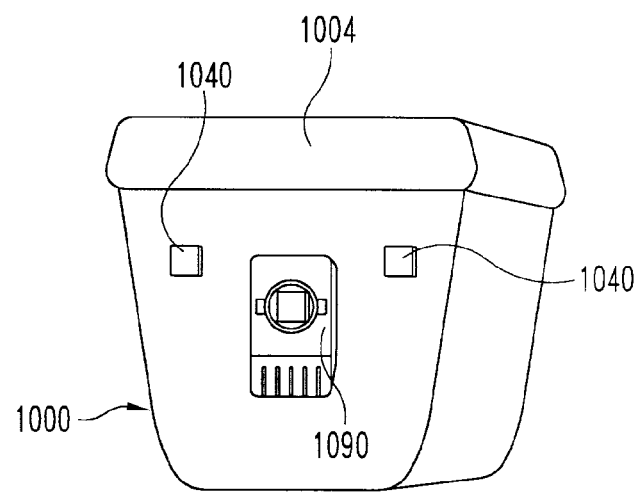
FIG. 24 illustrates a side view of the embodiment of FIG. 18 with the code key latch rotated to lock the container unless attached to a meter.

The stand-alone configuration of the container 1000 is illustrated in FIG. 24. To utilize the biosensor container 1000 as an attaching unit, the code key 1090 can be reinserted into the code key opening 1030 and rotated 90 degrees downward. This will rotate the locking plate 1022 into the locked position. The code key 1090 is also preferably designed as the latch to allow the container 1000 to be attached and locked to the meter (not illustrated), and without it the container 1000 cannot be attached to the meter (similar to the previously discussed features of FIGS. 10-13). When the biosensor container 1000 is attached to the meter, in one embodiment the meter body will depress two by-pass unlock buttons 1040 that push against the locking plate 1022 to allow the container lid 1004 to unlock (no interference of the lip 1026 to the latch).

Various embodiments of the above description refer to the code key as having data stored thereon relating to the glucose test strips. As previously mentioned, the data stored thereon preferably includes at least one, and even more preferably both, of the strip lot and strip family specific calibration information. Other examples of such information include, but are not limited to, calibration values, analyte ID, manufacturing date, expiration date, number of strips, and combinations of such information types. Furthermore, it should be understood that it is contemplated as within the scope of the invention that the code key include additional data storage capacity. Thus, the bG meter preferably can write additional information onto the code key. Such additional information might include, but is not limited to, information about the number of strips used, the bG result, the time and date of the test, information about the meter status, any error codes received during, before, or after testing. The additional information might further include any additional data being input into the meter manually or through other data input mechanisms provided on the bG meter. Examples of such additional data include insulin or carbohydrate data, or information about the user such as name, date of birth, or even insurance related information. Such data might be used, for example, for diagnostic purposes in case of malfunctions. Such data can also be downloaded to a health care professional's computer for further medical related analysis. Alternatively, such data might be downloaded to an insurer for participation in reward or discount programs based on compliance with care plans.

Various aspects of automating strip insertion into the meter, as well as automating the code key information delivery exist. However, existing devices do not allow for stand-alone operation. Particularly in systems that use one strip at a time, the lot calibration information transfer relied primarily, if not totally, on user interaction, thus making this step a candidate for failures. The more complex solutions with packages inside of the meter also typically require a complex, expensive device, that might result in high numbers of failures because of larger number of components needed (such as motors, logic, more mechanical parts, etc.) and with user problems and frustration.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. A biosensor container comprising:
a casing defining a compartment for receiving a plurality of glucose test strips;
means for storing data having, at least one of strip lot information and strip family specific calibration information stored thereon, wherein the means for storing data is sized to be at least partially received within and detachably connected to an engagement portion of the casing;
means for dispensing the glucose test strips only when the container is in either of a first mode or a second mode, and in the first mode the means for storing data is connected to the casing and the casing is docked to a meter, and in the second mode the means for storing data is detached from the casing and the casing is not docked to the meter;
wherein at least one of the casing and the means for storing data includes at least one data reading element that is externally accessible when the means for storing data is connected to the engagement portion of the casing, the at least one data reading element communicating with the means for storing data to access the data stored thereon.

2. The biosensor container of claim 1, wherein the compartment is pre-filled with a first batch of glucose test strips from the factory, and the data stored on the means for storing data includes calibration information for the first batch of glucose test strips.

3. The biosensor container of claim 1, wherein the compartment is externally accessible to fill the compartment with a plurality of glucose test strips.

4. The biosensor container of claim 1, in combination with the meter, and wherein the data stored on the means for storing data is automatically transferred from the means for storing data to the meter in the first mode.

5. The biosensor container of claim 4, in combination with the meter, and wherein the glucose test strips are directly dispensed into the meter in the first mode.

6. The biosensor container of claim 1, in combination with the meter, and wherein the casing is configured so that it can only be attached to the meter when the means for storing data is connected to the casing.

7. The biosensor container of claim 1, in combination with the meter, and wherein the means for storing data includes additional data storage capacity, and wherein the meter writes information onto the additional data storage capacity, the information being selected from the group consisting of number of strips used, bG results from at least one of the test strips, time and date of bG results, meter status, any error codes received during or before or after bG testing, and additional data manually input into the meter.

8. An apparatus comprising:
a bG meter;
a biosensor container comprising a casing defining an interior volume for a batch of glucose test strips;
means for storing data with data stored thereon relating to the batch of glucose test strips, the data including at least one of strip lot information and strip family specific calibration information, the means for storing data being separably connected to the biosensor container;
wherein the container is configured to only dispense glucose test strips when the container is in either of an attached-to meter mode or a stand-alone mode. and in the attached-to-meter mode the means for storing data is connected to the container and the container is connected to the bG meter. and in the stand-alone mode the means for storing data is separated from the container and the container is not connected to the bG meter.

9. The apparatus of claim 8, wherein the data stored on the means for storing data is automatically transferred from the means for storing data to the bG meter in the attached-to-meter mode.

10. The apparatus of claim 9. wherein the biosensor container includes means for dispensing the glucose test strips directly into the meter in the attached-to-meter mode.

11. The apparatus of claim 10, wherein the container is configured so that it can be attached to the bG meter only when the means for storing data is connected to the container.

12. The apparatus of claim 9, wherein the casing of the biosensor container defines an externally accessible portal that may be opened to fill the compartment with glucose test strips.

13. The apparatus of claim 12, wherein the means for storing data includes additional data storage capacity, and wherein the bG meter writes information onto the additional data storage capacity, the information being selected from the group consisting of number of strips used, bG results from at least one of the test strips, time and date of bG results, meter status, any error codes received during or before or after bG testing, and additional data manually input into the meter.

* * * * *